United States Patent [19]
Buck et al.

[11] Patent Number: 5,897,504
[45] Date of Patent: Apr. 27, 1999

[54] ULTRASOUND IMAGING PROBE ASSEMBLY

[75] Inventors: Arthur Glen Buck, Sherwood; Eric Evan Eichelberger, Tualatin; Doris Arlene Beck, Beaverton, all of Oreg.

[73] Assignee: The Whitaker Corporation, Wilmington, Del.

[21] Appl. No.: 08/989,902

[22] Filed: Dec. 12, 1997

[51] Int. Cl.⁶ ..................................................... A61B 8/00
[52] U.S. Cl. ............................................................. 600/463
[58] Field of Search .................................... 600/459, 462, 600/463, 466, 467, 443

[56] References Cited

U.S. PATENT DOCUMENTS 5,158,086  10/1992  Brown et al. .......................... 128/662
5,413,107  5/1995  Oakley et al. .......................... 128/662
5,445,155  8/1995  Sieben et al. ........................... 600/443

*Primary Examiner*—George Manuel
*Attorney, Agent, or Firm*—Gerald K. Kita

[57] ABSTRACT

An ultrasound imaging probe assembly (2) has control cables (13, 14) extending along an inner core (5) of a cable assembly (1), an ultrasound imaging transducer assembly (1') connected with signal transmitting conductors (10) in the inner core (5), the cable assembly (1) having a compression resistant armor (6) slidably receiving the inner core (5), the inner core (5) having respective sheaths (11) receiving the control cables (13, 14) and the signal transmitting conductors (10) in the inner core (5) urge the control cables (14) along respective orthogonal axes centered on a central axis of the cable assembly (1).

18 Claims, 3 Drawing Sheets

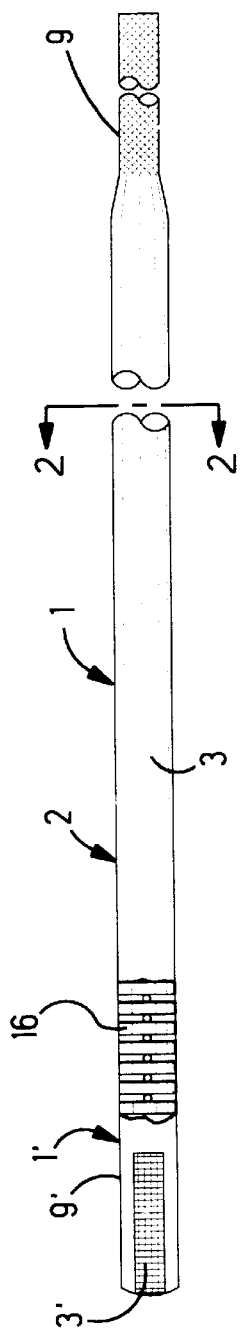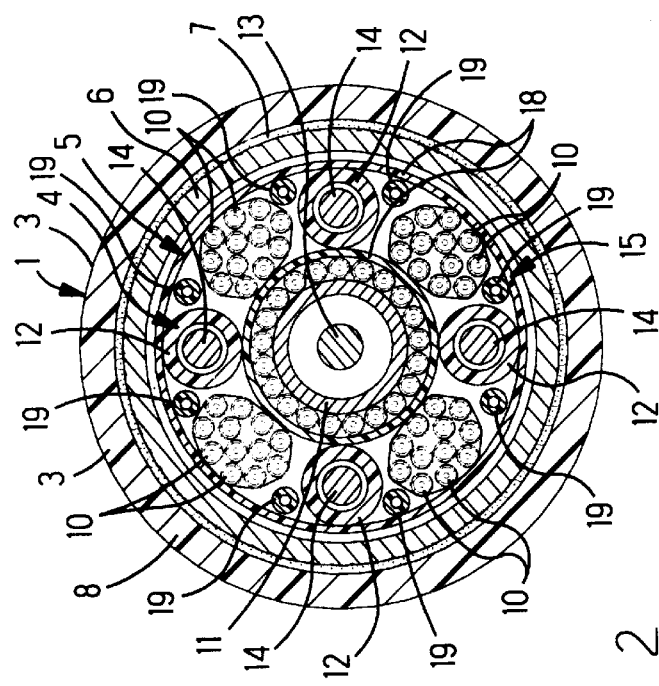

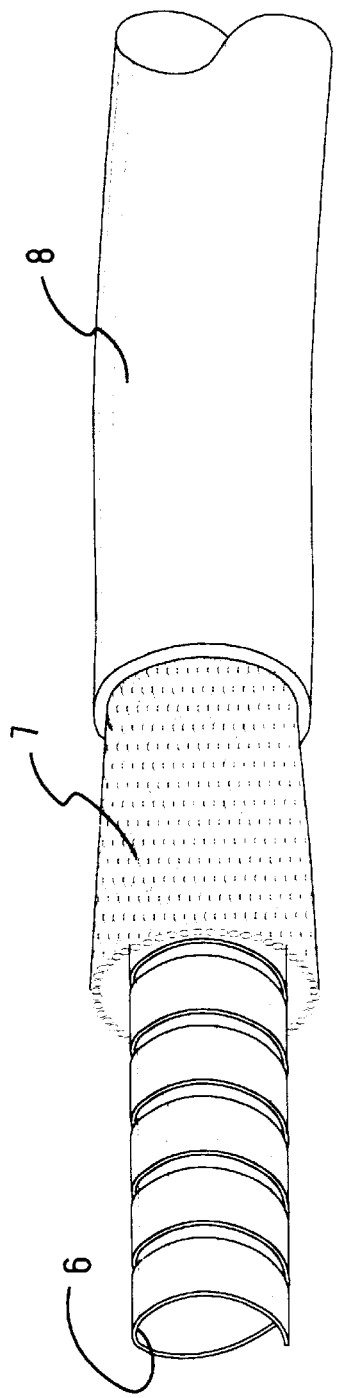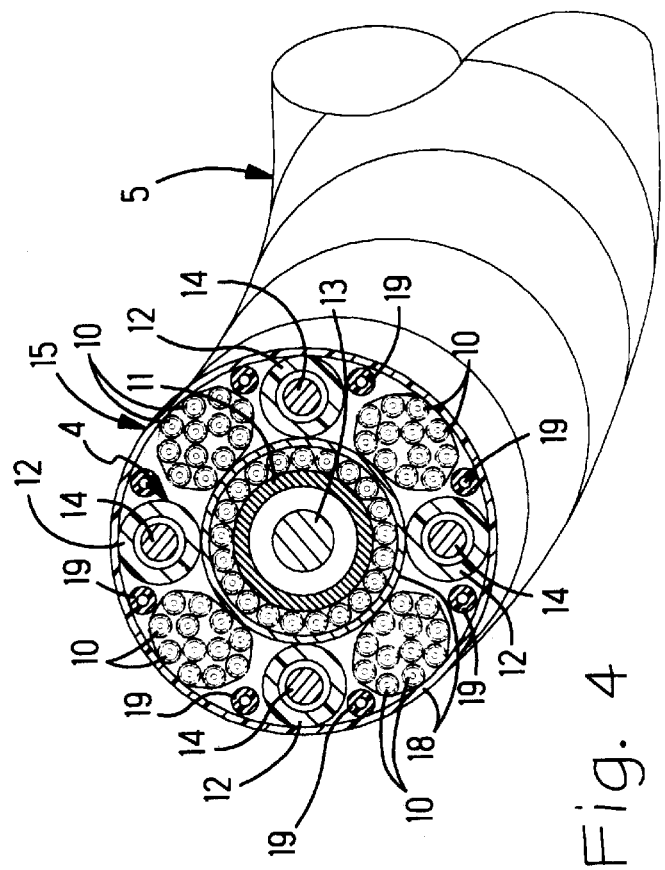

ULTRASOUND IMAGING PROBE ASSEMBLY

FIELD OF THE INVENTION

The invention relates to an ultrasound imaging probe assembly having an ultrasound transducer assembly rotatably mounted on an articulation link.

BACKGROUND OF THE INVENTION

U.S. Pat. No. 5,413,107, describes an ultrasound imaging probe. The probe has a probe assembly that comprises an ultrasonic transducer mounted rotatably on a distal end of a series of articulation links for flexure in different directions. The probe assembly is flexed by a cable drive that has an articulation control cable connected to the articulation links. Tension applied by the cable moves the articulation links to flex the probe assembly. The transducer is connected to signal transmitting electrical conductors to provide a transducer assembly. Ultrasonic waves from the transducer is reflected from a probed area of a medical patient. The transducer converts reflected ultrasonic waves to scanned electrical signals that are channeled along the signal transmitting conductors to apparatus that creates a scanned video image of the probed area. Clarity and definition of the image is increased by increasing the number of signal transmitting conductors, and consequently increasing the number of channels, for transmitting the scanned signals.

Increasing the number of signal transmitting conductors has, in the past, caused a corresponding increase in the size of the transducer assembly and the size of the cable assembly that contains the cable drive and the signal transmitting conductors. Particularly, the cable assembly and the transducer assembly must remain compact in size for non-injurious entry into a human body cavity, for example, an esophageal cavity, defined by human tissue. In the past, an ultrasound imaging probe assembly having both a cable drive and signal transmitting conductors has been difficult to construct in a compact size.

Further, a probe extended along an esophageal cavity is subject to damage by reflexive biting by a medical patient. U.S. Pat. No. 5,158,086 describes a probe according to which articulation control cables are proximate a center axis of a probe to avoid damage to the cables by reflexive biting by a medical patient. A desired probe is one that is adapted to avoid damage to the signal transmitting conductors, as well as to the control cables.

SUMMARY OF THE INVENTION

The terminology, probe assembly, referred to herein, refers to a portion of an ultrasound imaging probe, which comprises an ultrasonic transducer mounted rotatably on a distal end of a series of articulation links for flexure in different directions An ultrasound imaging probe assembly according to the invention comprises an outer sheath that resists harsh sterilization environments and resists damage by compression due to reflexive biting and rough handling, and an inner core that contains both, a cable drive to manipulate a ultrasound imaging probe, and multiple signal transmitting conductors transmitting scanned signals for diagnostic imaging of a probed area of a medical patient. The inner core is advantageously pulled through the outer sheath to provide a compact size.

An embodiment of the invention will now be described by way of example with reference to the accompanying drawings, according to which:

DESCRIPTION OF THE DRAWINGS

FIG. 1a is a top view of a ultrasound imaging probe assembly and a cable assembly, with an articulation portion partially cut away to show articulation links;

FIG. 2 is a section view of the cable assembly as shown in FIG. 1;

FIG. 3 is a top view of an outer sheath of the cable assembly as shown in FIGS. 1a and 2, with portions partially separated for illustration purposes; and FIG. 4 is a top view of an inner core of the cable assembly as shown in FIGS. 1a and 2, with portions partially separated for illustration purposes.

DETAILED DESCRIPTION

Figure 1:
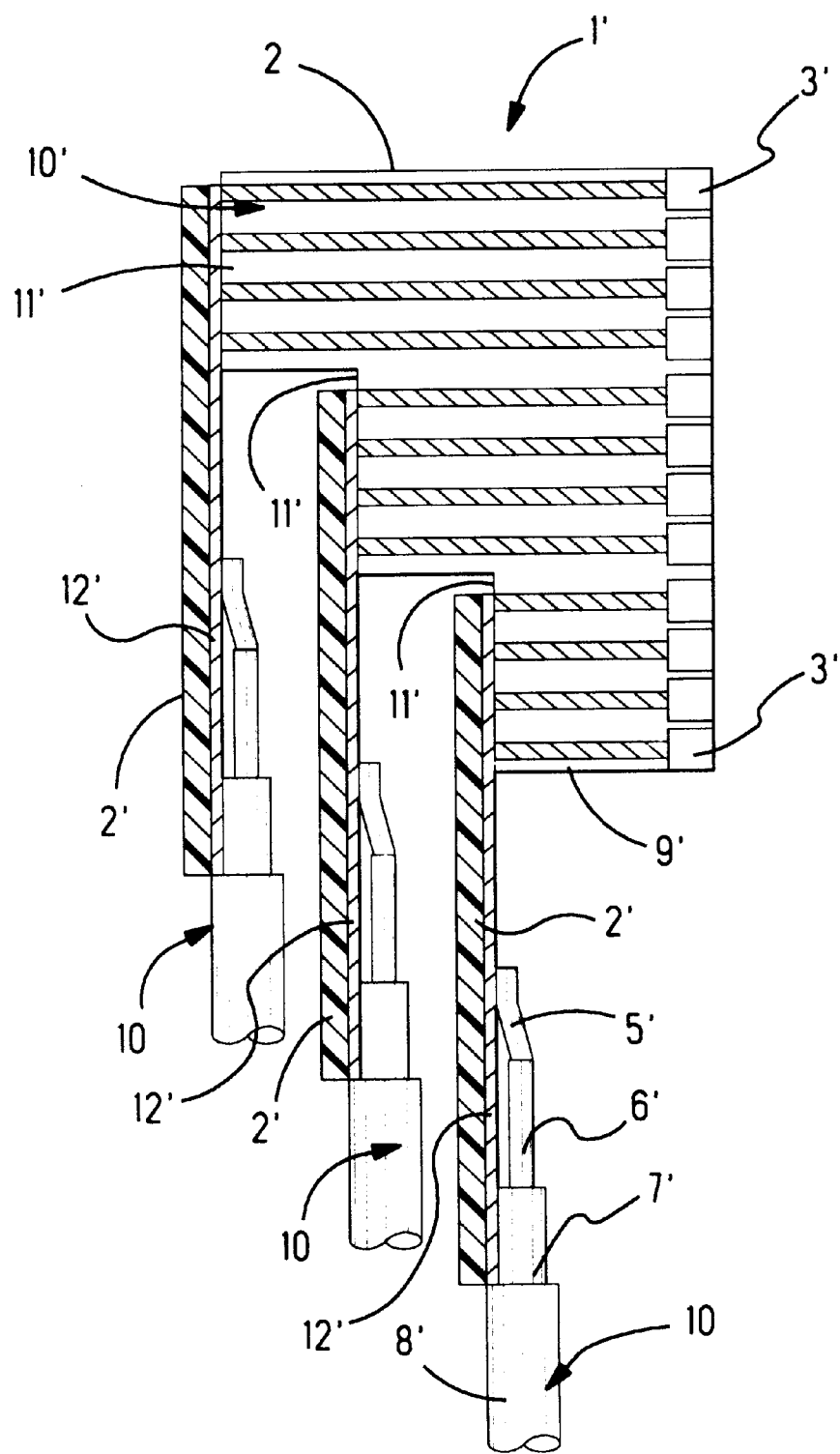
FIG. 1 is a side view in section of a portion of an ultrasound transducer assembly of an ultrasound imaging probe assembly, wherein, piezoelectric elements are electrically connected to signal transmitting conductors.

With reference to FIG. 1, an ultrasound imaging transducer assembly 1' of an ultrasound imaging probe assembly 2, FIG. 1a, comprises, circuitry 2' electrically connecting rows of piezoelectric elements 3' to signal transmitting conductors 10. The probe assembly 2 is hand held and manipulated to position the imaging transducer assembly 1' at a desired location on a medical patient. Pulsed ultrasound signals are transmitted along the assembly 1' to a medical instrument comprising, apparatus that scans the signals to produce an electronically generated image of a portion of the medical patient that is being probed. Each signal transmitting conductor 10 is a coaxial cable having a central conductor 5' concentrically within an encircling dielectric 6', in turn, concentrically within a conducting shield 7', in turn, concentrically within an encircling insulating jacket 8'. The piezoelectric elements 3 are mounted against a backing layer 9', developed as a wide variety of adhesive epoxy materials having a wide variety of fillers, that eliminate cross talk among the piezoelectric elements 3'. The backing material 9' can be molded or machined on a back side 10' of the backing material 9' with one or more steps. The steps have risers 11' corresponding to the side-to-side spacing of elements 3'. The printed circuits 2' can be made thin enough to not exceed the step height, typical of diagnostic ultrasound, with circuit trace centerlines as closely spaced as 4 mils. For example, the steps can be made in increments of 4 mil. height, measured from one step to another. The printed circuit 2', manufactured by etching an insulating substrate, can produce circuit traces 12' spaced apart on a pitch spacing as low as 4 mil. pitch spacing. Further details of the imaging transducer assembly 1' is described in U.S. patent application Ser. No. 08/959,870, filed Oct. 29, 1997, attorney docket 16841, incorporated herein by reference.

With reference to FIGS. 2–4, a cable assembly 1 extending along the cable driven ultrasound imaging probe assembly 2, FIGS. 1a and 2, comprises, an outer sheath 3, a cable drive 4 and an inner core 5. With reference to FIG. 3, the outer sheath 3 comprises, a metal strip helically wound and providing a hollow metal tube armor 6, a tubular conducting braided sheath shield 7 surrounding the metal tube armor 6 and a continuous impervious layer 8 enclosing the braided sheath shield 7. The outer sheath 3 is compression resistant due to the armor 6 to avoid damage by reflexive biting by a medical patient, as well as, by rough handling of the probe assembly 2. The braided sheath shield 7 is fabricated from slender wire strands, tin plated, and braided into a tubular sleeve form by conventional wire braiding machines. The braided sheath shield 7 provides EMI/RFI electrical shielding for electrical signal transmitting conductors that are enclosed by the braided sheath shield 7. According to the embodiment, the braided sheath shield 7 is external to, or on an outside of, the metal tube armor 6, which laterally supports the exterior of the helical wraps of the metal tube armor 6, and prevents the helical wraps from unwinding. The braided sheath shield 7 permits the helical wraps of the metal tube armor 6 to provide a self supporting hollow interior space, lined by the helical wraps, within which the inner core 5 is inserted with ease. Yet the sheath shield 7 provides electrical shielding within the interior of the sheath shield 7.

With reference to FIGS. 2 and 3, the braided sheath shield 7 has interstices among individual wire strands. A continuous impervious layer 8 encloses the braided sheath shield 7, and is comprised of an outer layer of polymeric material embedded in the interstices. The impervious layer 8 seals the cable assembly 1, and resists sterilization chemicals and sterilization environments typically in an autoclave with high temperature steam for a duration of time. A stub end 9, FIG. 1a, of the cable assembly 1 extends for connection and attachment to a remainder of the ultrasound imaging probe assembly 2, according to further details, which are disclosed by way of example in U.S. Pat. No. 5,413,107, incorporated herein by reference.

With reference to FIGS. 2 and 4, the inner core 5 comprises, the cable drive 4 and multiple slender strands of signal transmitting conductors in the form of coaxial cables 10. The inner core 5 further comprises, an elongated and slender first tunnel or sheath 11 having a central axis, and elongated and slender additional tunnels or sheaths 12. A first, rotatable torque control cable 13 of said cable drive 4 is rotatably received in the first tunnel or sheath 11. Additional, articulation control cables 14 of said cable drive 4 are axially slidable within said additional tunnels or sheaths 12.

The inner core 5 further comprises, said coaxial cables 10 extending axially in respective spaces separating the first tunnel or sheath 11 and the additional tunnels or sheaths 12 from one another. The inner core 5 further comprises, a sleeve 15 of polymeric material that readily slides within the hollow metal tube armor 6 of the outer sheath 3. The sleeve 15 encloses said tunnels or sheaths 11, 12 and said coaxial cables 10, in a compact bundle. The coaxial cables 10 are shown in FIG. 4 to be separated among multiple bundles. The signal transmitting conductors 10 within respective bundles are between two control cables 14 urging the control cables 14 toward their positions along respective orthogonal axes that are centered on a central axis of the cable assembly 1. Each of the bundles is helically wrapped with a loosely coiled length of a thin polytetrafluoroethylene tape. Although the bundles are shown in FIGS. 1a and 4, for purposes of illustration, with spaces between the bundles and the control cables 14, the coaxial cables 10 are more closely packed against the control cables 14, than as shown in FIGS. 1a and 4.

The sleeve 15 is advantageously of a slippery 15 material such that the bundle, comprising the sheaths 11, 12 and the signal transmitting conductors in the form of coaxial cables 10, is slidable with low frictional resistance inside the metal tube armor 6 of the outer sheath 3, accordingly, to provide a compact cable assembly 1.

The cables 13 and 14 are attached, respectively, to the transducer assembly 1' and the articulation links 16 in a known manner as disclosed in U.S. Pat. No. 5,158,086 and U.S. Pat. No. 5,413,107. The transducer assembly 11 is rotatably mounted on the articulation links 16 in a known manner as disclosed in U.S. Pat. No. 5,158,086 and U.S. Pat. No. 5,413,107. By applying tension on alternate ones of each pair of the additional cables 14 of the cable drive 4, such pair of cables 14 will traverse slidably within the tunnels or sheaths 12, exerting flexure forces on the articulation links 16, FIG. 1, of the bendable portion of the ultrasound imaging probe assembly 2, to which the cables 14 are attached, to move the articulation links 16 by flexure relative to two orthogonal axes of movement. Further details of the articulation links 16 are disclosed in U.S. Pat. No. 5,413,107. The sheaths 12 are spaced from a central axis of the inner core 5 of the cable assembly 1 to provide a relatively large moment arm to maximize the force applied to flex the articulation links 16 relative to the central axis.

The closely packed, coaxial cables 10 in the bundle laterally support said additional tunnels or sheaths 12 along orthogonal axes centered on the central axis of the first tunnel 11. The orthogonal spacing of the additional tunnels or sheaths 12, and of the cables 14 within the additional tunnels or sheaths 12, is maintained by the closely packed, coaxial cables 10, and without mechanical struts, thereby saving space. The orthogonal spacing of the additional tunnels or sheaths is maintained with the passage of time, such that the same amount of tension applied to the cables 14 results in the same relative movement of the articulation links 16.

The cable assembly 1 is of multiple part construction, one distinct part comprising the outer sheath 3, and another distinct part comprising, the inner core 5. Advantageously, the inner core 5 is pulled through the outer sheath 3 to result in a finished cable assembly 1. The outer sheath 3 is hollow cylindrical. The inner core 5 is a smaller cylinder comprised of a bundle of closely packed together cables that comprise, a cable drive 4 to manipulate the ultrasound imaging probe assembly 2, as well as, multiple signal transmitting conductors in the form of the coaxial electrical cables 10 transmitting scanned signals for diagnostic imaging of a probed area of a medical patient. This multiple part construction allows for a cable assembly 1 of reduced diameter, making it ideally compact for insertion along a cavity defined by human tissue. Current cable assemblies are 19 mm diameter with less than 40 channels of scanned signals along 40 corresponding electrical cables. A cable assembly 1 according to the invention is 17 mm diameter, and has 69 channels of scanned signals along 69 corresponding signal transmitting conductors comprising the electrical cables 10. A larger number of channels provides greater resolution of an electronically created image.

The outer sheath 3 comprises a hollow conducting armor 6 of a helically wrapped stainless steel band encircled by the tubular conducting braided sheath shield 7. The stainless steel band has a rectangular cross section 0.010×0.250 inches. The braided sheath shield 7 is 40 American Wire Gauge. The braided sheath shield 7 is imbedded in the impervious layer 8 fabricated as an extruded outer layer of polyurethane, medical grade rating, USP, Class VI, adding 0.012 inch thickness. The finished outer diameter is 0.279 inch, 7.08 mm, diameter. The braided sheath shield 7 has 90% coverage, and 10% interstices into which the outer layer 8 imbeds to provide an impervious probe assembly 2 for containing the inner core 5.

The inner core 5 is pulled through the outer sheath 3. The inner core 5 is built with a central, hollow conducting tunnel or sheath 11 of helically wrapped spring stainless steel stock 0.016 thick, with an outer diameter of 0.072 inch, and an inner diameter of 0.056 inch. A first cable 13, of the cable drive 4, of 0.052 inch diameter is inserted along the tunnel or sheath 11, and is freely rotatable within the enclosing tunnel or sheath 11, for example, providing a rotatable torque control cable to rotate the ultrasound imaging transducer assembly 1', FIG. 1, mounted on a distal end or tip of the ultrasound imaging probe assembly 2, FIG. 1a.

The inner core 5 is built with a row of closely packed coaxial cables 10 distributed against the exterior periphery of the central tunnel 11. The row of said cables 10 is held against the central tunnel 11 by helically wound wraps of tape 18, of 0.002 inch thin polytetrafluoroethylene, with a 45% overlap of adjacent wraps. A multiple number of cables 10 in a compact space is obtained.

The inner core 5 is built with four additional, control line tunnels or sheaths 12 angularly spaced apart and along orthogonal axes centered on the central axis of the central tunnel 11. Each of the additional tunnels or sheaths 12 is fabricated with a helically wrapped ribbon of spring stainless steel stock 0.016 thick, with an outer diameter of 0.043 inch, and an inner diameter of 0.027 inch. Each of the additional cables 14 of the cable drive 4 is a round wire cable of 0.018 inch diameter, and is inserted along a corresponding additional tunnel or sheath 12, and is freely slidable, back an forth, within the enclosing tunnel or sheath 12, for example, providing an articulation control cable 14 that alternately will curve and straighten the articulation links 16 of the probe assembly 2, as the cables 14 are reciprocating, moved back and forth.

The spaces that separate the control line tunnels or sheaths 12 are packed with closely packed coaxial cables 10, followed by helical wraps of 0.002 inch thick polytetrafluoroethylene tape 18, with a 45 overlap of adjacent wraps, resulting in the sleeve 15 that surrounds and compacts a cylindrical bundle of the electrical cables 10 and the cable drive 4 that will readily slide for assembly within the outer sheath 3. By being closely packed, the coaxial cables 10 will retain the spacing apart of the control line tunnels or sheaths 12 in place, over passage of time, along orthogonal axes centered on the central axis of the central tunnel 11. The lengths of the cables 14 must remain a constant with respect to the length of the cable assembly 1 to insure a minimum amount of play when tensioning the cables 14.

Each of the signal transmitting conductors is a coaxial cable 10 that is constructed of a central conductor, 42 American Wire Gauge, surrounded by a concentric dielectric of 7/50 polytetrafluoroethylene having a 0.0028 inch nominal wall, in turn, surrounded by a concentric conducting shield of 48 American Wire Gauge TC served wires with 95% minimum coverage. An outer jacket is fabricated with 0.0025 H.S. polyester tape that is helically wrapped with 40% nominal overlap of adjacent wraps.

Alternatively, each of the signal transmitting conductors 10 comprises an insulated conductor 10 capacitively coupled with an inner conductor and an outer conductor, wherein the inner conductor is helically encircled by multiple ones of the insulated conductor 10, and the outer conductor concentrically encircles the multiple ones of the insulated conductor 10, as described in U.S. Provisional Application Serial Number, unknown, filed Nov. 25, 1997, attorney docket number 17122L, incorporated herein by reference.

Alternatively, multiple insulated wires 19 to conduct electrical power are together with the coaxial cables 10, and are distributed in pairs adjacent to each of the additional tunnels or sheaths 12. The insulated wires are, for example, fabricated as 36 American Wire Gauge 7/44, insulated by 0.004 nominal wall thickness polytetrafluoroethylene. The insulated wires 19 connect to a motor control apparatus for the probe assembly 2, according to further details described in patent Application Ser. No. unknown, filed Dec. 10, 1997, attorney docket 17113, entitled, Navigable Ultrasound Imaging Probe Assembly, Inventors, Eric Evan Eichelberger and Arthur Glen Buck, incorporated herein by reference.

Although an embodiment of the invention has been described, other embodiments and modifications are intended to be covered by the spirit and scope of the appended claims.

What is claimed is:

1. An ultrasound imaging probe assembly comprising: an ultrasound imaging transducer mounted on articulation links, said transducer being connected to multiple signal transmitting conductors, at least a pair of reciprocating articulation control cables connected to said articulation links, a rotatable torque control cable connected to said transducer, a cable assembly having an inner core, respective sheaths in said inner core receiving said control cables, said signal transmitting conductors being received in said inner core, and said cable assembly having an outer sheath, said outer sheath having a compression resistant armor within a braided wire shield, and a polymeric layer covering said shield and imbedding in interstices of said shield.

2. An ultrasound imaging probe assembly as recited in claim 1 wherein, said inner core has a sleeve of polymeric material that readily slides for assembly within said armor, said sleeve enclosing said signal transmitting conductors and said respective sheaths in a compact bundle.

3. An ultrasound imaging probe assembly as recited in claim 1 wherein, said armor is a helically wound metal strip providing a hollow metal tube.

4. An ultrasound imaging probe assembly as recited in claim 1 wherein, said armor is a helically wound metal strip providing a hollow metal tube, and said inner core has a sleeve of polymeric material that readily slides for assembly within said armor, and said sleeve encloses said signal transmitting conductors and said respective sheaths in a compact bundle.

5. An ultrasound imaging transducer .assembly for an ultrasound imaging probe, as recited in claim 1, and further comprising: at least one row of closely packed coaxial cables distributed against an exterior periphery of a central one of the respective sheaths, and said row being held against the central tunnel by tape, whereby a maximum number of said coaxial cables in a compact space is obtained.

6. An ultrasound imaging transducer assembly for an ultrasound imaging probe comprising:

an ultrasound imaging transducer connected to multiple signal transmitting conductors, a rotatable torque control cable connected to said transducer, a cable assembly having an inner core, a respective sheath in said inner core receiving said control cable, said signal transmitting conductors being received in said inner core, and said cable assembly having an outer sheath, said outer sheath having a compression resistant armor within a braided wire shield, and a polymeric layer covering said shield and imbedding in interstices of said shield.

7. An ultrasound imaging transducer assembly for an ultrasound imaging probe, as recited in claim 6, and further comprising: at least one row of closely packed coaxial cables distributed against an exterior periphery said respective sheath, and said row being held against said respective sheath by tape, whereby a maximum number of said coaxial cables in a compact space is obtained.

8. An ultrasound imaging transducer assembly for an ultrasound imaging probe, as recited in claim 6 wherein, said armor is a helically wound metal strip providing a hollow metal tube.

9. An ultrasound imaging transducer assembly for an ultrasound imaging probe, as recited in claim 6 wherein, said armor is a helically wound metal strip providing a hollow metal tube, and said inner core has a sleeve of polymeric material that readily slides for assembly within said armor, and said sleeve encloses said signal transmitting conductors and said respective sheaths in a compact bundle.

10. An ultrasound imaging transducer assembly for an ultrasound imaging probe, as recited in claim 6, and further comprising: said inner sheath having articulation control cables in additional respective sheaths.

11. An ultrasound imaging transducer assembly for an ultrasound imaging probe, as recited in claim 6, and further comprising: said inner sheath having articulation control cables in additional respective sheaths radially spaced from a central axis of said cable assembly, and said signal transmitting conductors urging said additional respective sheaths along respective orthogonal axes centered on said central axis.

12. A cable assembly connecting an ultrasound imaging transducer and an ultrasound imaging probe assembly, comprising:

an outer sheath extending along said probe assembly, said outer sheath having a compression resistant armor within a braided wire shield, and a polymeric layer covering said shield and imbedding in interstices of said shield, and an inner sheath within said outer sheath, said inner sheath having multiple signal transmitting conductors connected to the transducer, a rotatable torque control cable connected to the transducer and a respective sheath receiving said control cable.

13. A cable assembly connecting an ultrasound imaging transducer and an ultrasound imaging probe assembly, as recited in claim 12, and further comprising: said inner sheath having articulation control cables in additional respective sheaths.

14. A cable assembly connecting an ultrasound imaging transducer and an ultrasound imaging probe assembly, as recited in claim 12, and further comprising: said inner sheath having articulation control cables in additional respective sheaths radially spaced from a central axis of said cable assembly, and said signal transmitting conductors urging said additional respective sheaths along respective orthogonal axes centered on said central axis.

15. A cable assembly connecting an ultrasound imaging transducer and an ultrasound imaging probe assembly, as recited in claim 12, and further comprising: elongated insulated wires supplying electrical power along said cable assembly, said insulated wires extending along said inner sheath.

16. A cable assembly connecting an ultrasound imaging transducer and an ultrasound imaging probe assembly, comprising:

an outer sheath extending along said probe assembly, said outer sheath having a compression resistant armor within a braided wire shield, and a polymeric layer covering said shield and imbedding in interstices of said shield, and an inner sheath within said outer sheath, said inner sheath having multiple signal transmitting conductors connected to the transducer, said inner sheath having articulation control cables in respective sheaths radially spaced from a central axis of said cable assembly, and said signal transmitting conductors urging said respective sheaths along respective orthogonal axes centered on said central axis.

17. A cable assembly connecting an ultrasound imaging transducer and an ultrasound imaging probe assembly, as recited in claim 16, and further comprising: elongated insulated wires supplying electrical power along said cable assembly, said insulated wires extending along said inner sheath.

18. A cable assembly connecting an ultrasound imaging transducer and an ultrasound imaging probe assembly, as recited in claim 16, and further comprising: said inner core has a sleeve of polymeric material that readily slides for assembly within said armor, said sleeve enclosing said signal transmitting conductors and said respective sheaths in a compact bundle.

* * * * *